Patented Apr. 25, 1944 Plant Pat. 625

UNITED STATES PATENT OFFICE

625

SEEDLESS NAVEL ORANGE TREE

Donald John Nicholson, Orlando, Fla.

No Drawing. Application December 3, 1941, Serial No. 421,526

1 Claim. (Cl. 47—62)

The new and distinct variety of seedless navel orange tree with its smaller-sized fruits, which is being described in this application, was first and originally discovered by me on October 5, 1939, in a small citrus grove planted to mixed varieties, among which were found about 15 other navel orange trees, none of which produced fruits of the character found on the parent tree—the one with which this application deals. In some respects, the fruits produced on some of these other trees did, in a general way, resemble the type of fruit borne by the tree discovered and selected for patenting. While some of the other navel trees found in this grove produced fruits of strikingly similar outward appearance they differed in the interior construction, juice-content, flavor, maturity season, etc., and none possessed the remarkable flavor and allround high quality found in variety herein being described.

The tree was found by accident as I walked around in the grove; its fruits were so well-colored that I was at once attracted to the tree by this precociousness, since navels in Florida rarely show so much color upon this early date. Upon cutting and examining the fruit, I was most agreeably surprised to find them extremely juicy and fully matured and of remarkable flavor.

I thereupon cut some budwood from the heaviest-bearing branches producing the finest-looking fruits, and I used this budwood for propagating on young sweet orange and sour orange seedlings and, in addition, for top-working buds into limbs of an old bearing grapefruit tree. Since then the buds have reproduced fruits identical to those found on the parent tree. At the time of the discovery I had some misgivings as to whether this tree would repeat this performance, but subsequent events have proven my fears were groundless—the tree having since twice repeated this behavior, bearing fruits true to the type first found.

In spite of six weeks of abnormally cold weather during the fall of 1939, this tree began to put out a few blooms on December 30, 1939, but very few; then the severe 15-day freeze came in January–February 1940, delaying heavy blooming until March 19th, when it was found covered profusely with "pin-point" blossoms. Despite this greatly retarded bloom, the fruits were found to be maturing and of good flavor and heavy juice-content by the first week in October, however, not quite as mature as previous season. Again the following November 15, 1940, another severe freeze came and once more affected its normal blooming period—it did not bloom until the last week in March, setting a large crop of fruits which also matured by the first week in October. And it might be stated here that the tree was in no way injured by cold and seemingly hardy.

This hardy navel tree is, perhaps, 25 or 30 years of age and is a budded tree on undetermined rootstock. Rather slender-trunked with a well-shaped symmetrical top, resembling somewhat any ordinary seedling orange tree. It fruits heavily, producing both on inside wood and from top to bottom on outside twigs and branches. For three consecutive seasons it has borne big crops of fruits ranging in size from 150's to 250's, and averaging size 200. The fruits are smooth and thin-skinned, symmetrical of shape and specimens are rarely found with protruding navel.

Parent tree is thornless. Progeny buds are thornless; however, a few of these progencies have been found producing thorns.

A most interesting and significant feature is the early chemical analyses of the fruits tested for three consecutive seasons between October 2nd and October 17th. These comparative tests made by competent fruit men show the following results:

Juice content 5½ to 6.14 gallons of juice per box from fruits of any size-range produced by this navel. 33% to 45% higher juice content than was found in any other standard early Florida varieties of oranges between October 2nd and October 17.

Solids ranged from 11.10 to 11.75 between the period of October 2nd and October 17th.

Ratio of sugars to acid for same period was from 10.50 to one, to 14.62 to one, averaging 4½ to 5 points higher than that found in other early-type Florida oranges.

A more detailed description follows:

*Description of fruit.*—Form somewhat variable, varying from round or nearly round to slightly oblate, either somewhat tapering towards apex or with apex flat; size small, medium and large, averaging size 200's (Florida standard packed box basis); color orange or orange-yellow; apex terminating in an umbilicus, either set in flat surface or tapering outward, small or wide opening; navel small, rarely extending very far into fruit; base rounded, rather smooth, sometimes creased; calyx small; stem small; rind thin, very smooth, sometimes satin-like, medium tough, not leathery, about ¼ inch thick; oil cells small;

sections vary from 8 to 13, usually 10 or 11, well defined; flesh very fine-grained, orange-yellow; juice-sacs small, slender and narrow; juice extremely abundant, never showing a particle of dryness in any parts of fruit; pulp tender and melting, no rag; acidity and sweetness remarkably well-blended; flavor a delicious combination of rare blending from very first maturity and throughout maturity period; quality excellent; seeds absent in majority of fruits, some, however, with one or more seeds (January normal-bloom crops remarkably free of seeds, 60 to 70% of crop with seeds entirely absent); season October first to January when by mid-month fruits become very ripe.

*Notation.*—A remarkable feature about the skin of this orange is its ability to apparently retain its citrus oils. Specimens cut cross-section can be eaten out of hand with little or no annoyance from mouth burns or sting, whether due to the absence of certain constituents usually present in citrus oils or retention of the oils themselves is not certain.

I claim:

A new and distinct variety of navel orange tree substantially as described, characterized particularly by its much heavier juice content; its larger amount of acidity; its absence of dry juice-cells and ability to hold its juices; its higher ratios of sugars to acids; its higher content of soluble solids; its different flavor; its shorter maturing period after flowering, which is 6 to 6½ months; and its higher rate of productivity on sour orange rootstock; all as compared with the Washington navel orange.

DONALD JOHN NICHOLSON.